US012597483B2

(12) United States Patent
Wen et al.

(10) Patent No.: US 12,597,483 B2
(45) Date of Patent: Apr. 7, 2026

(54) MOLECULAR DOCKING METHOD AND APPARATUS BASED ON COHERENT ISING MACHINE

(71) Applicant: BEIJING QBOSON QUANTUM TECHNOLOGY CO., LTD., Beijing (CN)

(72) Inventors: Kai Wen, Beijing (CN); Yin Ma, Beijing (CN)

(73) Assignee: BEIJING QBOSON QUANTUM TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/851,870

(22) PCT Filed: Mar. 24, 2023

(86) PCT No.: PCT/CN2023/083567
§ 371 (c)(1),
(2) Date: Nov. 6, 2024

(87) PCT Pub. No.: WO2023/185658
PCT Pub. Date: Oct. 5, 2023

(65) Prior Publication Data
US 2025/0166724 A1     May 22, 2025

(30) Foreign Application Priority Data
Mar. 28, 2022    (CN) ......................... 202210310733.X

(51) Int. Cl.
*G16B 15/30* (2019.01)
*G16C 20/50* (2019.01)

(52) U.S. Cl.
CPC ............. *G16B 15/30* (2019.02); *G16C 20/50* (2019.02)

(58) Field of Classification Search
CPC ................................ G16B 15/30; G16C 20/50
See application file for complete search history.

(56) References Cited

U.S. PATENT DOCUMENTS

| | | |
|---|---|---|
| 2009/0081701 A1 | 3/2009 | Cen |
| 2019/0369097 A1 | 12/2019 | Fiser et al. |
| 2021/0193273 A1 | 6/2021 | Miller |

FOREIGN PATENT DOCUMENTS

| | | |
|---|---|---|
| CN | 110289055 A | 9/2019 |
| CN | 112543943 A | 3/2021 |
| CN | 112786122 A | 5/2021 |
| CN | 114120006 A | 3/2022 |
| CN | 114882940 A | 8/2022 |
| JP | 2005018447 A | 1/2005 |
| WO | 2019104440 A1 | 6/2019 |

OTHER PUBLICATIONS

Honarparvar, B., Govender, T., Maguire, G. E., Soliman, M. E., & Kruger, H. G. (2014). Integrated approach to structure-based enzymatic drug design: molecular modeling, spectroscopy, and experimental bioactivity. Chemical reviews, 114(1), 493-537. (Year: 2014).*
Banchi L, Fingerhuth M, Babej T, Ing C, Arrazola JM. Molecular docking with Gaussian Boson Sampling. Sci Adv. Jun. 5, 2020;6(23): eaax1950. doi: 10.1126/sciadv.aax1950. PMID: 32548251; PMCID: PMC7274809. (Year: 2020).*
Ahmed, Sinthyia, et al. "Investigating the binding affinity, interaction, and structure-activity-relationship of 76 prescription antiviral drugs targeting RdRp and Mpro of SARS-CoV-2."J Biomol Struct Dyn. Oct. 2021;39(16):6290-6305. doi: 10.1080/07391102.2020. 1796804. Epub Jul. 28, 2020. PMID: 32720571 (Year: 2021).*
Haribara, Y., 2017. Realization and Evaluation of Measurement Feedback Coherent Ising Machines for Combinatorial Optimization Problems. U. Tokyo dissertation. 107 pages (Year: 2017).*
Takehara, Kota, et al. "A multiple coefficients trial method to solve combinatorial optimization problems for simulated-annealing-based ising machines." 2019 IEEE 9th International Conference on Consumer Electronics (ICCE-Berlin). IEEE, 2019. (Year: 2019).*
Dutta, S., Khanna, A., Paik, H., Schlom, D., Raychowdhury, A., Toroczkai, Z. and Datta, S., 2020. An Ising Hamiltonian Solver using Stochastic Phase-Transition Nano-Oscillators. arXiv preprint arXiv:2007.12331. (Year: 2020).*
Firoz A. Dain Md Opo, et al., Structure based pharmacophore modeling, virtual screening, molecular docking and ADMET approaches for identification of natural anti-cancer agents targeting XIAP protein, Scientific Reports, 2021, vol. 11 No.4049.
Hongzhao Wang, et al., Classification models and SAR analysis on CysLT1 receptor antagonists using machine learning algorithms, Molecular Diversity 2021, pp. 1597-1616, vol. 25.
Leonardo Banchi, et al., Molecular docking with Gaussian Boson Sampling, Sci. Adv., 2020, pp. 1-9, vol. 6, eaax1950.
Leonardo Banchi, et al., Training Gaussian Boson Sampling Distributions, 2020, pp. 1-15.

(Continued)

*Primary Examiner* — Karlheinz R. Skowronek
*Assistant Examiner* — Nidhi Dharithreesan
(74) *Attorney, Agent, or Firm* — Bayramoglu Law Offices

(57) ABSTRACT

A molecular docking method based on a CIM includes: constructing a 3D molecular structure diagram based on a selected drug molecule to obtain a ligand graph; constructing an internal pseudo-atom point diagram of a receptor target based on a selected receptor molecule to obtain a receptor graph; constructing a ligand-receptor similarity graph based on the ligand graph and the receptor graph, where the ligand-receptor similarity graph includes vertices and edges between any two vertices, and any vertex of includes a point in the ligand graph and a point in the receptor graph; determining whether each edge exists; and constructing a pharmacophore model based on the ligand-receptor similarity graph to determine whether the selected drug molecule could inhibit activity of the selected receptor, where the pharmacophore model is configured to calculate a maximum weight clique between the selected drug molecule and the selected receptor to screen a drug molecule compound.

9 Claims, 15 Drawing Sheets

(56)         References Cited

OTHER PUBLICATIONS

Guillaume Chapuis, et al., Finding Maximum Cliques on the D-Wave Quantum Annealer, Journal of Signal Processing Systems, 2019, pp. 363-377 No.91.
Kevin Mato, et al., Quantum Molecular Unfolding, 2021, pp. 1-12.
Jinyin Zha, et al., Encoding Molecular Docking for Quantum Computers, J. Chern. Theory Comput., 2023, pp. 9018-9024, vol. 19.

* cited by examiner

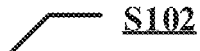

Select a drug molecule from a drug molecule library to be screened, and construct a 3D molecular structure diagram based on the selected drug molecule to obtain a ligand graph

Select a receptor from a receptor library, and construct an internal pseudo-atom point diagram of a receptor target based on the selected receptor molecule to obtain a receptor graph

Construct a ligand-receptor similarity graph based on the ligand graph and the receptor graph, where the ligand-receptor similarity graph includes a plurality of vertices and edges, and any vertex of the plurality of vertices includes a point in the ligand graph and a point in the receptor graph

Construct a pharmacophore model based on the ligand-receptor similarity graph to determine whether the selected drug molecule could inhibit activity of the selected receptor, where the pharmacophore model is configured to calculate a maximum weight clique between the selected drug molecule and the selected receptor to screen a drug molecule compound

Node 1    Node 2    Node 3    Node 4    Node 5    Node 6    Node 7    Node 8    Node 9
(L1,R1)   (L1,R2)   (L1,R3)   (L2,R1)   (L2,R2)   (L2,R3)   (L3,R1)   (L3,R2)   (L3,R3)

MOLECULAR DOCKING METHOD AND APPARATUS BASED ON COHERENT ISING MACHINE

CROSS REFERENCE TO THE RELATED APPLICATIONS

This application is the national phase entry of International Application No. PCT/CN2023/083567, filed on Mar. 24, 2023, which is based upon and claims priority to Chinese Patent Application No. 202210310733.X, filed on Mar. 28, 2022, the entire contents of which are incorporated herein by reference.

TECHNICAL FIELD

The present disclosure relates to the technical field of drug design, and in particular to a molecular docking method and apparatus based on a coherent Ising machine (CIM).

BACKGROUND

Traditional drug screening is a very expensive and resource-intensive process, typically costing billions of dollars, with a success rate of about 10%. In recent years, with the development of powerful molecular modeling tools and the increasing number of analytical structures for protein-micromolecule complexes, structure-based drug design has become an essential tool in new drug development. The focus of molecular docking research is to simulate the molecular recognition process through calculations, aiming to simulate the optimal pose between proteins and ligands so as to minimize the free energy of the entire system. As a crucial task in the early stage of drug screening, molecular docking can accelerate the drug development process.

When molecular docking is conducted on traditional computers, different algorithms are usually used to explore and sample the pose space, and the binding state is evaluated through a scoring function. The commonly used software includes Genetic Optimisation for Ligand Docking (GOLD), Autodock Vina (VINA), etc.

In the pharmaceutical field, traditional models mostly use heuristic algorithms and system search algorithms for screening, which are time-consuming and may not be able to obtain optimal solutions, resulting in high false positive rate in the drug development process. The heuristic algorithms and system search algorithms have the following drawbacks:

(1) The heuristic algorithms take a long time for iteration, but they may not be able to obtain the optimal solution, and have high computational load.

(2) The system search algorithms may encounter the problem of combination explosion, and traditional computers are not competent in handling such problems.

Traditional models require a large amount of sampling to generate a low-energy pose, but the pose may not be the global optimal solution. The present disclosure uses a model that features higher solving efficiency and faster speed than traditional methods.

SUMMARY

In view of the above analysis, embodiments of the present disclosure provide a molecular docking method and apparatus based on a coherent Ising machine (CIM). The present disclosure solves the problems that traditional heuristic algorithms are time-consuming but may not be able to obtain standard solutions, etc.

In an aspect, an embodiment of the present disclosure provides a molecular docking method based on a coherent Ising machine (CIM), including: selecting a drug molecule from a drug molecule library to be screened, and constructing a three-dimensional (3D) molecular structure diagram based on the selected drug molecule to obtain a ligand graph; selecting a receptor from a receptor library, and constructing an internal pseudo-atom point diagram of a receptor target based on the selected receptor molecule to obtain a receptor graph; constructing a ligand-receptor similarity graph based on the ligand graph and the receptor graph, where the ligand-receptor similarity graph includes a plurality of vertices and edges, any vertex of the plurality of vertices includes a point in the ligand graph and a point in the receptor graph, and there is an edge between any two vertices; determining whether each edge exists; and constructing a pharmacophore model based on the ligand-receptor similarity graph to determine whether the selected drug molecule could inhibit activity of the selected receptor, where the pharmacophore model is configured to calculate a maximum weight clique between the selected drug molecule and the selected receptor to screen a drug molecule compound.

The above technical program has the following beneficial effects. In the present disclosure, the pharmacophore model constructed according to the ligand-receptor similarity graph is faster and more accurate in solving molecular simulation problems. The pharmacophore model can calculate the maximum weight clique between the drug molecule and the receptor to screen the drug molecule compound and determine whether the selected drug molecule could inhibit the activity of the selected receptor.

As a further improvement based on the above method, the determining whether each edge exists includes determining whether there is an edge between any two vertices of the plurality of vertices by a distance between the two vertices.

As a further improvement based on the above method, determining whether there is the edge between any two vertices of the plurality of vertices by the distance between the two vertices includes: determining a first distance between a point in a ligand graph at a first vertex and a point in a ligand graph at a second vertex; determining a second distance between a point in a receptor graph at the first vertex and a point in a receptor graph at the second vertex; and determining that, when both the first distance and the second distance are less than a preset distance, the edge between any two vertices is added.

As a further improvement based on the above method, the preset distance is within a range of 0.1 angstroms-2 angstroms.

As a further improvement based on the above method, the maximum weight clique between the selected drug molecule and the selected receptor corresponds to a similarity of atoms between the selected drug molecule and the selected receptor.

As a further improvement based on the above method, the maximum weight clique between the selected drug molecule and the selected receptor is determined according to a following equation:

$$\sum_{i=1}^{m}\sum_{j=i}^{n} w_{(i,j)} x_{(i,j)} - K_1 \sum_{i,k=1}^{m}\sum_{j,l=1}^{n} w_{(i,j),(k,l)} x_{(i,j)}$$

where $w_{(i,j)}$ denotes weight of vertex $x_{(i,j)}$ in the ligand-receptor similarity graph, depending on a type of an atom/group corresponding to i,j; $w_{(i,j),(k,l)}$ denotes weight of an edge between $x_{(i,j)}$ and $x_{(k,l)}$ in the ligand-receptor similarity graph; and $K_1$ is coefficient of the maximum weight clique.

As a further improvement based on the above method, the pharmacophore model is solved according to a following equation:

$$\min\left(-\sum_{i=1}^{m}\sum_{j=1}^{n}w_{(i,j)}x_{(i,j)} + K_1\sum_{i,k=1}^{m}\sum_{j,l=1}^{n}w_{(i,j),(k,l)}x_{(i,j)} + K_2\sum_{i=1}^{m}(\sum_{j=1}^{n}x_{(i,j)} - s_1)^2 + \right.$$
$$\left. K_2\sum_{j=1}^{m}\left(\sum_{i=1}^{n}x_{(i,j)} - s_1\right)^2 + K_3\left(\sum_{i=1}^{m}\sum_{j=1}^{n}x_{(i,j)} - (s_3 + 2s_4 + 4S_5 + 3)\right)^2\right)$$

where $w_{(i,j)}$ denotes the weight of the vertex $x_{(i,j)}$ in the ligand-receptor similarity graph, depending on the type of the atom/group corresponding to i,j; $w_{(i,j),(k,l)}$ denotes the weight of the edge between $x_{(i,j)}$ and $x_{(k,l)}$ in the ligand-receptor similarity graph; $K_1$ is the coefficient of the maximum weight clique; and $K_2$ and $K_3$ are Lagrange coefficients used to constrain a number of connections of a node and a number of solutions.

As a further improvement based on the above method, the selected receptor includes a protein, a nucleic acid or a polysaccharide; and the selected drug molecule includes aspirin, oseltamivir or remdesivir.

In another aspect, an embodiment of the present disclosure provides a molecular docking apparatus based on a CIM, including: a ligand selection module, configured to select a drug molecule from a drug molecule library to be screened; a ligand graph construction module, configured to construct a 3D molecular structure diagram based on the selected drug molecule to obtain a ligand graph; a receptor selection module, configured to select a receptor from a receptor library; a receptor graph construction module, configured to construct an internal pseudo-atom point diagram of a receptor target based on the selected receptor molecule to obtain a receptor graph; a ligand-receptor similarity graph construction module, configured to construct a ligand-receptor similarity graph based on the ligand graph and the receptor graph, where the ligand-receptor similarity graph includes a plurality of vertices and edges, any vertex of the plurality of vertices includes a point in the ligand graph and a point in the receptor graph, and there is an edge between any two vertices; the ligand-receptor similarity graph construction module is further configured to determine whether each edge exists; and a pharmacophore model, configured to construct a pharmacophore model based on the ligand-receptor similarity graph to determine whether the selected drug molecule could inhibit activity of the selected receptor, where the pharmacophore model is configured to calculate a maximum weight clique between the selected drug molecule and the selected receptor to screen a drug molecule compound.

As a further improvement based on the above method, the ligand-receptor similarity graph construction module is further configured to determine whether there is an edge between any two vertices of the plurality of vertices by a distance between the two vertices; the ligand-receptor similarity graph construction module includes a first distance determination module, a second distance determination module, and an edge determination module; the first distance determination module is configured to determine a first distance between a point in a ligand graph at a first vertex and a point in a ligand graph at a second vertex; the second distance determination module is configured to determine a second distance between a point in a receptor graph at the first vertex and a point in a receptor graph at the second vertex; and the edge determination module is configured to determine that, when both the first distance and the second distance are less than a preset distance, the edge between any two vertices is added.

Compared with the prior method, the present disclosure has at least one of the following beneficial effects:

1. In the present disclosure, the pharmacophore model constructed according to the ligand-receptor similarity graph is faster and more accurate in solving molecular simulation problems. The pharmacophore model can calculate the maximum weight clique between the drug molecule and the receptor to screen the drug molecule compound and determine whether the selected drug molecule could inhibit the activity of the selected receptor.

2. The maximum weight clique between the selected drug molecule and the selected receptor corresponds to a similarity of atoms between the selected drug molecule and the selected receptor. In the present disclosure, the method of solving molecular simulation problems through the Ising model is faster and more accurate. Based on the entanglement and overlapping states and fully connected characteristics of the quantum computer, the present disclosure proposes a more excellent model for solving molecular binding modes. The model is displayed on the web and available for users to use.

3. In the pharmaceutical field, the present disclosure is more convenient and fast, and can obtain better potential pharmaceutical compounds.

The above technical solutions in the present disclosure can also be combined with each other to realize more preferred combination solutions thereof. Other features and advantages of the present disclosure will be described in the following specification, and some of these will become apparent from the specification or be understood by implementing the present disclosure. The objectives and other advantages of the present disclosure may be implemented or derived by those specifically indicated in the description and drawings.

BRIEF DESCRIPTION OF THE DRAWINGS

The drawings are provided merely for illustrating specific embodiments and are not considered as limiting the present disclosure. Throughout the drawings, the same reference numerals represent the same components.

FIG. 1 is a flowchart of a molecular docking method based on a coherent Ising machine (CIM) according to an embodiment of the present disclosure;

FIG. 2 is a two-dimensional (2D) molecular structure diagram of a selected drug molecule;

FIG. 3 is a three-dimensional (3D) molecular structure diagram of the selected drug molecule;

DETAILED DESCRIPTION OF THE EMBODIMENTS

Figure 4:
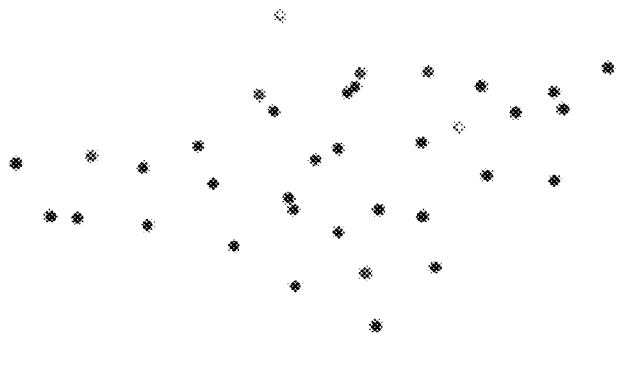
FIG. 4 is a schematic diagram of internal pseudo-atom points of a receptor target according to an embodiment of the present disclosure.

Preferred embodiments of the present disclosure will be described in detail below with reference to the drawings. The drawings constitute a part of the present disclosure, and are used together with the embodiments of the present disclosure for explaining principles of the present disclosure rather than for limiting a scope of the present disclosure.

A specific embodiment of the present disclosure provides a molecular docking method based on a coherent Ising machine (CIM). As shown in FIG. 1, the molecular docking method based on a CIM includes following steps. In step 102, a drug molecule is selected from a drug molecule library to be screened, and a three-dimensional (3D) molecular structure diagram is constructed based on the selected drug molecule to obtain a ligand graph. The ligand graph is circular and includes a plurality of atoms and edges in the drug molecule, with each edge being an edge between any two atoms. In step 104, a receptor is selected from a receptor library, and an internal pseudo-atom point diagram of a receptor target is constructed based on the selected receptor to obtain a receptor graph. The receptor graph is circular and includes a plurality of atoms and edges in a receptor molecule, with each edge being an edge between any two atoms. In step 106, a ligand-receptor similarity graph is constructed based on the ligand graph and the receptor graph. The ligand-receptor similarity graph includes a plurality of vertices and edges, where any vertex of the plurality of vertices includes a point in the ligand graph and a point in the receptor graph, and there is an edge between any two vertices. In this step, it is further determined whether each edge exists. In step S108, a pharmacophore model is constructed based on the ligand-receptor similarity graph to determine whether the selected drug molecule could inhibit activity of the selected receptor. The pharmacophore model is configured to calculate a maximum weight clique between the selected drug molecule and the selected receptor to screen a drug molecule compound. The receptor is a macromolecular substance that can recognize and selectively bind to a certain ligand (signaling molecule).

Compared with the prior method, the pharmacophore model constructed according to the ligand-receptor similarity graph in this embodiment is faster and more accurate in solving molecular simulation problems. The pharmacophore model can calculate the maximum weight clique between the drug molecule and the receptor to screen the drug molecule compound and determine whether the selected drug molecule could inhibit the activity of the selected receptor.

In the present disclosure, the method of solving molecular simulation problems based on the pharmacophore model is faster and more accurate.

As shown in FIGS. 1 to 8, the steps 102 to S108 of the molecular docking method based on a CIM are described in detail below according to an embodiment of the present disclosure.

Figures 2, 3:
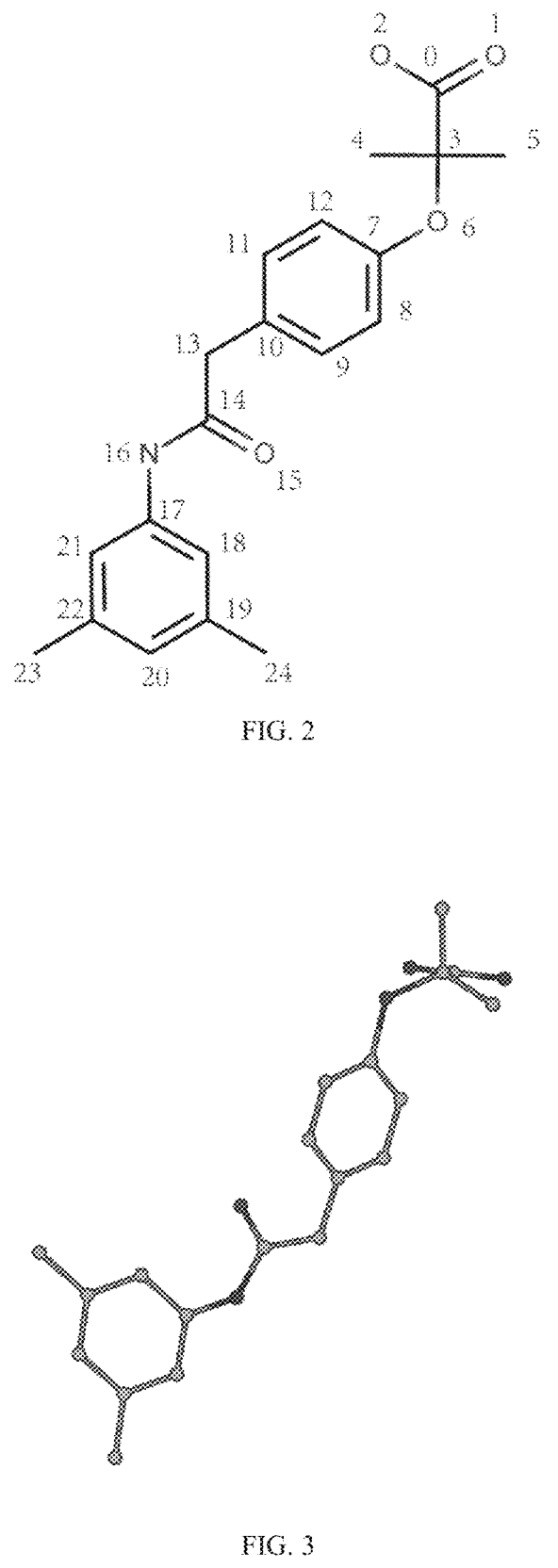

In the step 102, the drug molecule (as shown in FIG. 2) is selected from the drug molecule library to be screened, and the 3D molecular structure diagram (as shown in FIG. 3) is constructed based on the selected drug molecule to obtain the ligand graph. Specifically, the 3D molecular structure diagram (drug molecular structure diagram) is constructed based on the selected drug molecule, and then the ligand graph is generated based on the 3D molecular structure diagram. As shown in FIGS. 10B, 13B, and 16B, the ligand graph is circular and includes a plurality of atoms and edges in the drug molecule, with each edge being an edge between any two atoms. The selected drug molecule includes aspirin, oseltamivir or remdesivir, etc. For example, an inhibitor of MMP9, thiamine or biaryl succinic acid, etc. is selected from the drug molecule library to be screened.

Figure 5:
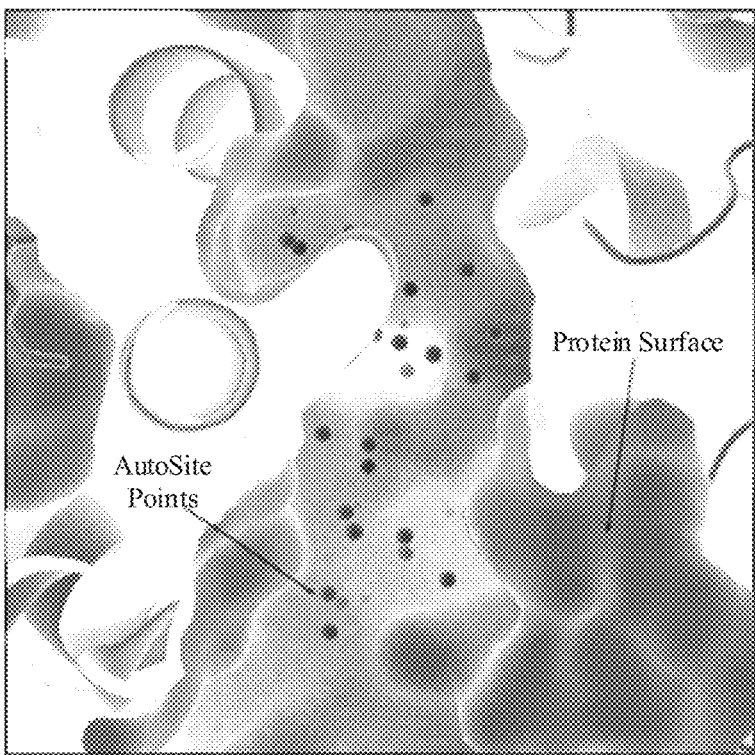
FIG. 5 is a pseudo-atom diagram of the pseudo-atom points and a protein target structure according to an embodiment of the present disclosure.
Figure 11A:
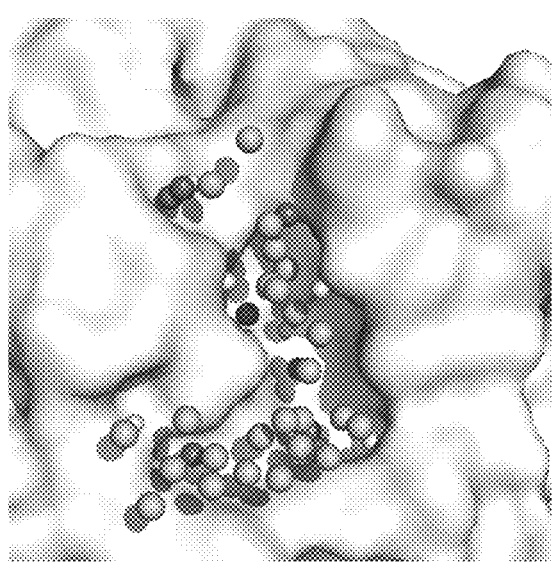
FIG. 11A is a pseudo-atom diagram according to the first specific example of the present disclosure.
Figure 11B:
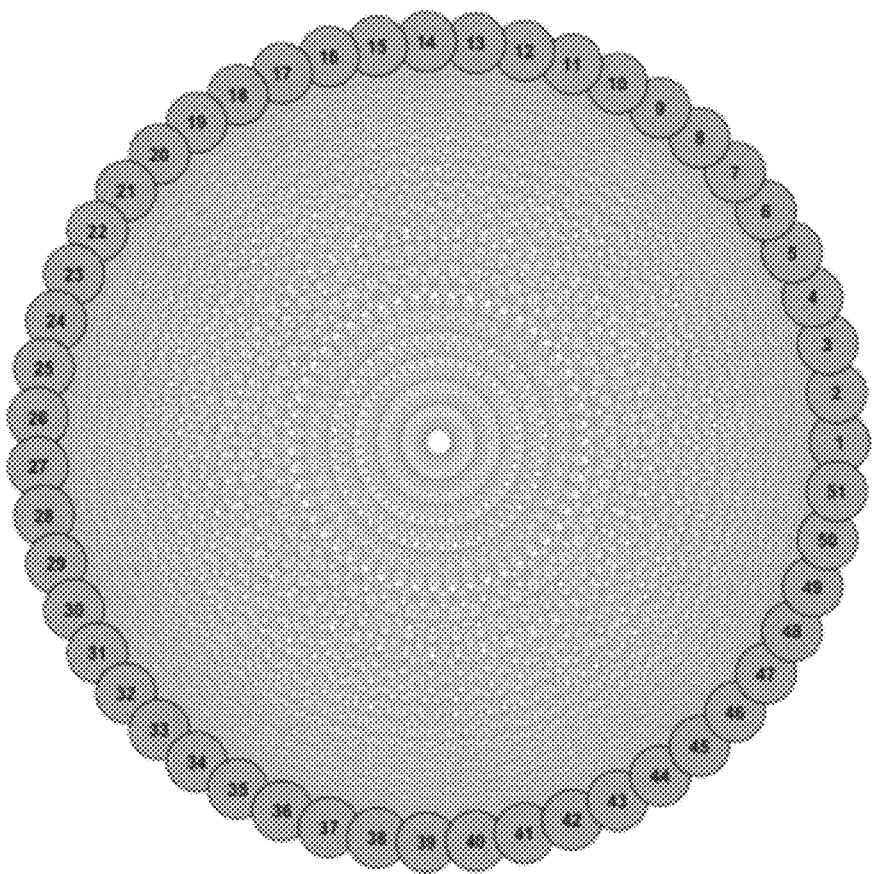
FIG. 11B is a receptor graph according to the first specific example of the present disclosure.
Figure 14A:
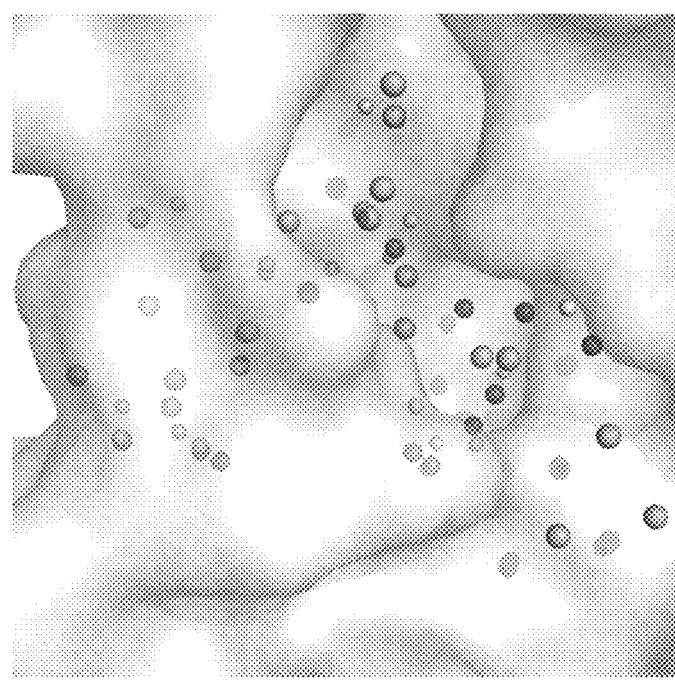
FIG. 14A is a pseudo-atom diagram according to the second specific example of the present disclosure.
Figure 14B:
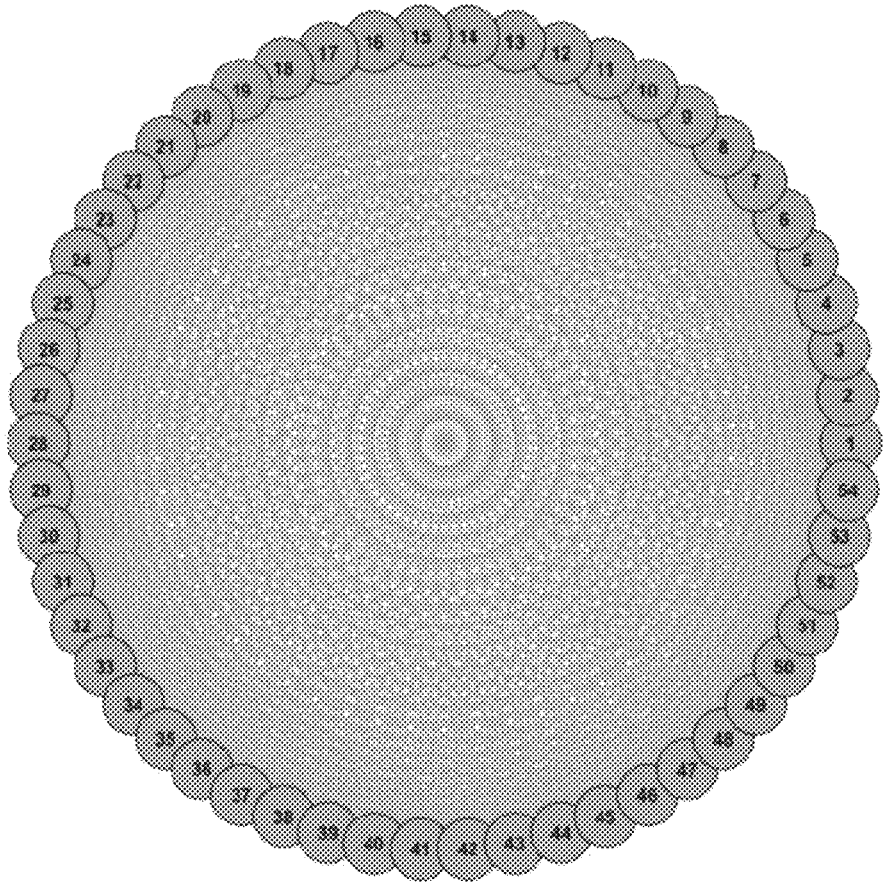
FIG. 14B is a receptor graph according to the second specific example of the present disclosure.
Figure 17A:
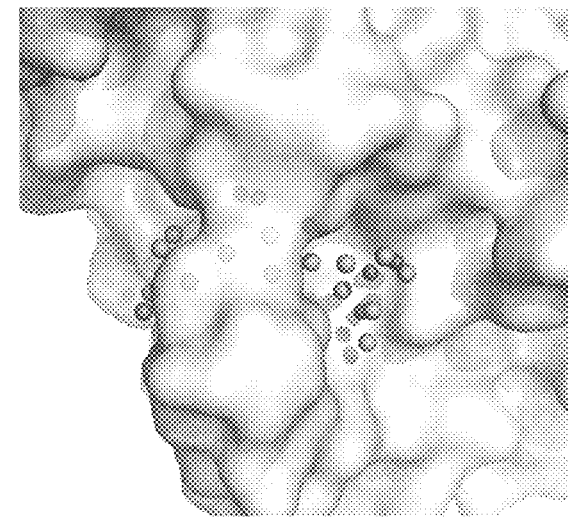
FIG. 17A is a pseudo-atom diagram according to the third specific example of the present disclosure.
Figure 17B:
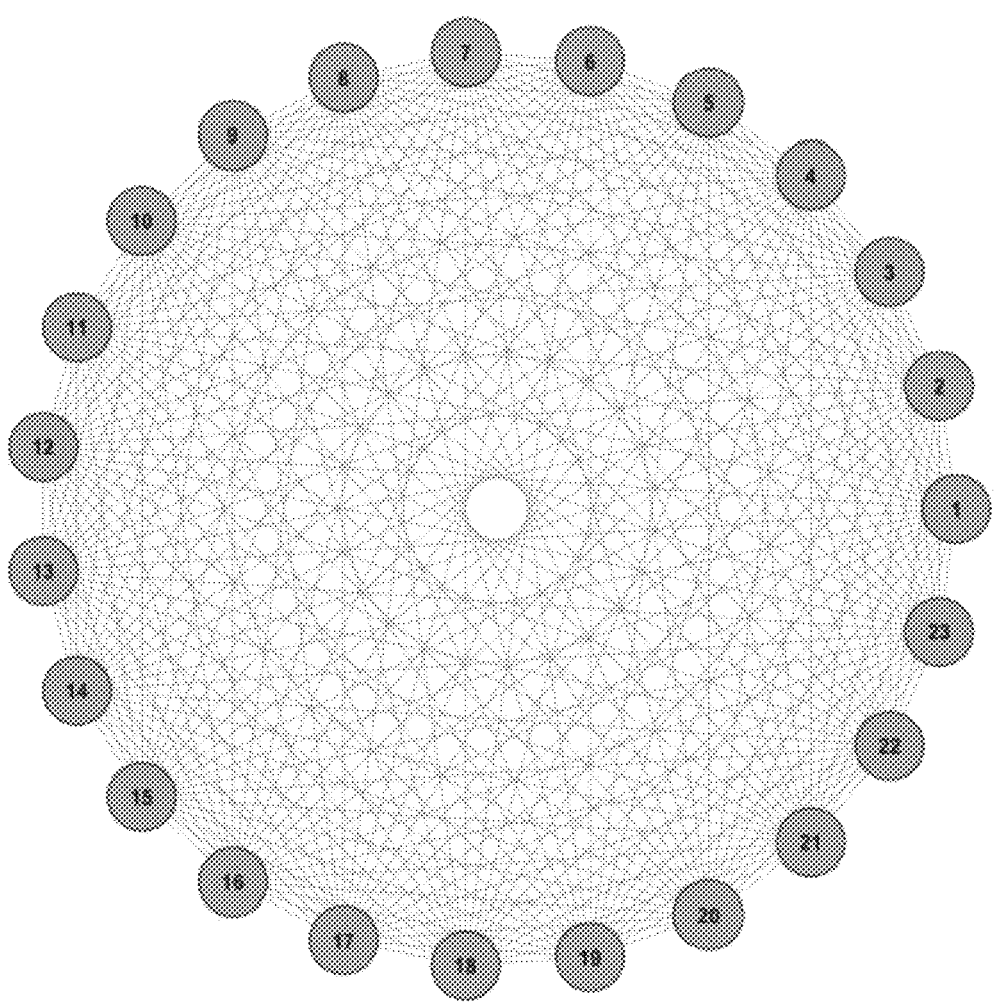
FIG. 17B is a receptor graph according to the third specific example of the present disclosure.

In the step 104, the receptor is selected from the receptor library, and the internal pseudo-atom point diagram (as shown in FIG. 4) of the receptor target is constructed based on the selected receptor molecular structure to obtain the receptor graph. Specifically, pseudo-atom points of the receptor are obtained through AutoSite software, and the receptor graph is obtained based on the pseudo-atom points. As shown in FIGS. 11B, 14B, and 17B, the receptor graph is circular and includes a plurality of atoms and edges in the receptor molecule, with each edge being an edge between any two atoms. The selected receptor includes a protein, a nucleic acid or a polysaccharide. For example, MMP9, mouse thiamine pyrophosphokinase, or IMP-1 metallo-β-lactamase from *Pseudomonas aeruginosa* is selected from the receptor library. FIG. 5 shows the pseudo-atom point diagram and pseudo-atom diagram of a protein target structure. For example, as shown in FIGS. 4 and 5, when the receptor is a protein, assuming that the pseudo-atom point is a point inside a protein cavity, the drug molecule is matched with the receptor to determine whether the selected drug molecule could inhibit the activity of the selected receptor.

Figure 6:
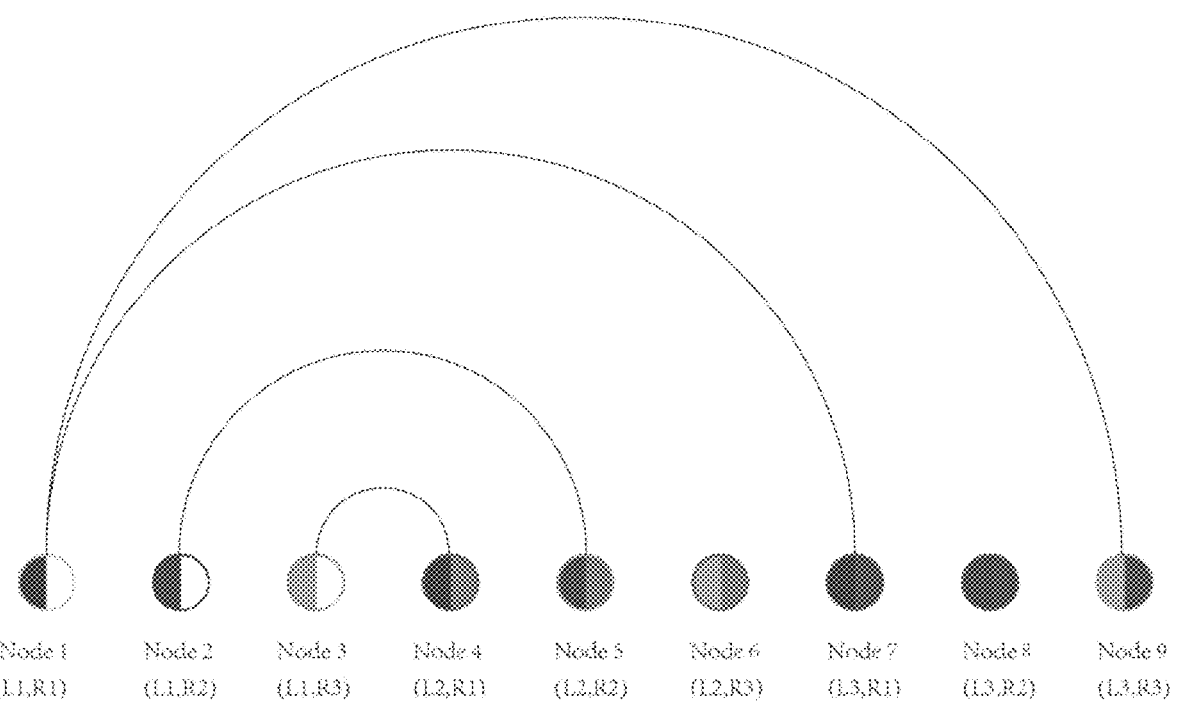
FIG. 6 is a schematic diagram of constructing vertices of a ligand-receptor similarity graph according to an embodiment of the present disclosure.

In the step 106, the ligand-receptor similarity graph is constructed based on the ligand graph and the receptor graph, and the ligand-receptor similarity graph includes a plurality of vertices and edges. As shown in FIG. 6, the plurality of vertices traverse all points in the ligand graph and the receptor graph, where any vertex includes a point in the ligand graph and a point in the receptor graph, and there is an edge between any two vertices. In this step, further, it is determined whether each edge exists. Specifically, in the step of determining whether each edge exists, it is further determined whether an edge exists between any two vertices of the plurality of vertices by a distance between the two vertices. In the step of determining whether there is the edge between any two vertices of the plurality of vertices by the distance between the two vertices, further, a first distance between a point in a ligand graph at a first vertex and a point in a ligand graph at a second vertex is determined; a second distance between a point in a receptor graph at the first vertex and a point in a receptor graph at the second vertex is determined; and when both the first distance and the second distance are less than a preset distance, it is determined that an edge between any two vertices is added. The preset distance is within a range of 0.1 angstroms-2 angstroms. In a preferred embodiment, the preset distance is within a range of 0.5 angstroms-1 angstroms.

Figure 7:
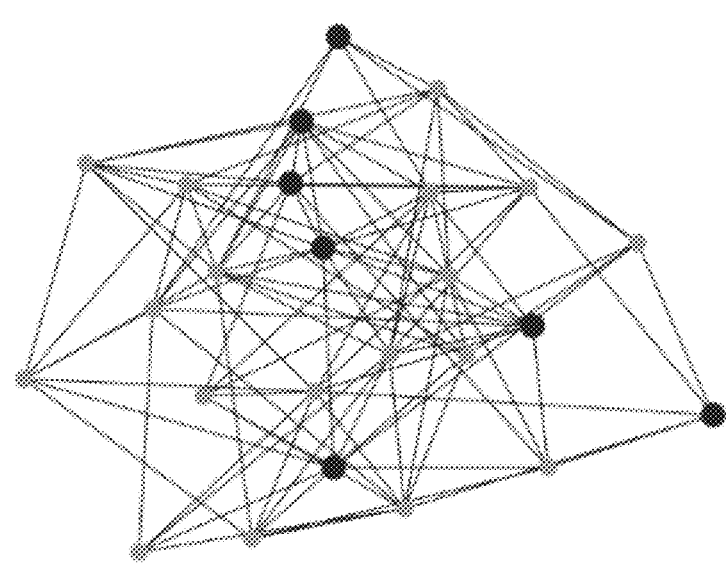
FIG. 7 is the ligand-receptor similarity graph according to an embodiment of the present disclosure.

In the step S108, the pharmacophore model is constructed based on the ligand-receptor similarity graph to determine whether the selected drug molecule could inhibit the activity of the selected receptor. The pharmacophore model is configured to calculate the maximum weight clique (also known as the maximum clique) between the selected drug molecule and the selected receptor to screen the drug molecule compound. Specifically, the maximum weight clique between the selected drug molecule and the selected receptor corresponds to a similarity of atoms between the selected drug molecule and the selected receptor. The maximum clique is usually one in a complete graph with a highest number of points found from an undirected graph. For example, as shown in FIG. 7, the maximum clique in the ligand-receptor similarity graph is a clique with a highest number of vertices in the ligand-receptor similarity graph.

The maximum weight clique between the selected drug molecule and the selected receptor is determined according to a following equation:

$$\sum_{i=1}^{m}\sum_{j=i}^{n}w_{(i,j)}x_{(i,j)} - K_1\sum_{i,k=1}^{m}\sum_{j,l=1}^{n}w_{(i,j),(k,l)}x_{(i,j)}$$

In the equation, $w_{(i,j)}$ denotes the weight of vertex $x_{(i,j)}$ in the ligand-receptor similarity graph, depending on a type of an atom/group corresponding to i,j, i.e. a similarity between two atoms. For example, the similarity between the two atoms in (C,C) is 1, and the similarity between the two atoms in (C,O) can be (0.8). $w_{(i,j),(k,l)}$ denotes the weight of an edge between $x_{(i,j)}$ and $x_{(k,l)}$ in the ligand-receptor similarity graph. If $x_{(i,j)}$ and $x_{(k,l)}$ are connected by an edge, then the weight of the edge is 1. If $x_{(i,j)}$ and $x_{(k,l)}$ are not connected by an edge, then the weight of the edges is 0. $K_1$ is a coefficient of the maximum weight clique, and $K_1$ can be manually adjusted.

The pharmacophore model is solved according to a following equation:

$$\min\left(-\sum_{i=1}^{m}\sum_{j=1}^{n}w_{(i,j)}x_{(i,j)} + K_1\sum_{i,k=1}^{m}\sum_{j,l=1}^{n}w_{(i,j),(k,l)}x_{(i,j)} + K_2\sum_{i=1}^{m}(\sum_{j=1}^{n}x_{(i,j)} - s_1)^2 + \right.$$
$$\left. K_2\sum_{j=1}^{m}(\sum_{i=1}^{n}x_{(i,j)} - s_1)^2\right) + K_3\left(\sum_{i=1}^{m}\sum_{j=1}^{n}x_{(i,j)} - (s_3 + 2s_4 + 4S_5 + 3)\right)^2\right)$$

In the equation, $w_{(i,j)}$ denotes the weight of the vertex $x_{(i,j)}$ in the ligand-receptor similarity graph, depending on the type of the atom/group corresponding to i,j; $w_{(i,j),(k,l)}$ denotes the weight of the edge between $x_{(i,j)}$ and $x_{(k,l)}$ in the ligand-receptor similarity graph; $K_1$ is the coefficient of the maximum weight clique; and $K_2$ and $K_3$ are Lagrange coefficients used to constrain a number of connections of a node and a number of solutions.

Figure 9:
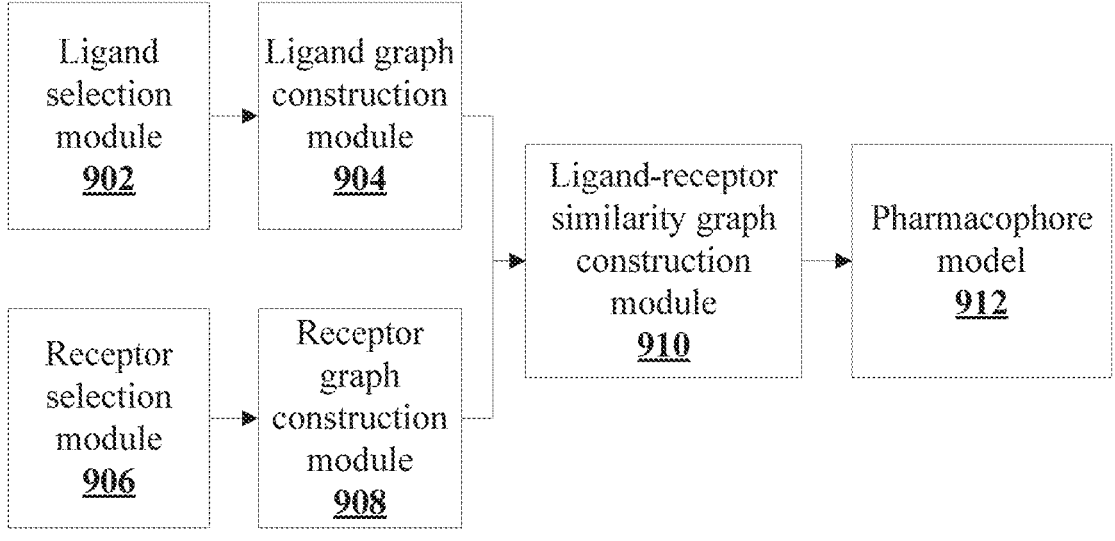
FIG. 9 is a block diagram of a molecular docking apparatus based on a CIM according to an embodiment of the present disclosure.

Another specific embodiment of the present disclosure provides a molecular docking apparatus based on a CIM. As shown in FIG. 9, the molecular docking apparatus based on a CIM includes: ligand selection module 902, ligand graph construction module 904, receptor selection module 906, receptor graph construction module 908, ligand-receptor similarity graph construction module 910, and pharmacophore model 912.

The ligand selection module 902 is configured to select a drug molecule from a drug molecule library to be screened. The ligand graph construction module 904 is configured to construct a 3D molecular structure diagram based on the selected drug molecule to obtain a ligand graph. The ligand graph is circular and includes a plurality of atoms and edges in the drug molecule, with each edge being an edge between any two atoms. The receptor selection module 906 is configured to select a receptor from a receptor library. The receptor graph construction module 908 is configured to construct an internal pseudo-atom point diagram of a receptor target based on the selected receptor molecule to obtain a receptor graph. The receptor graph is circular and includes a plurality of atoms and edges in the receptor molecule, with each edge being an edge between any two atoms. The ligand-receptor similarity graph construction module 910 is configured to construct a ligand-receptor similarity graph based on the ligand graph and receptor graph. The ligand-receptor similarity graph includes a plurality of vertices and edges, and any vertex of the plurality of vertices includes a point in the ligand graph and a point in the receptor graph. There is an edge between any two vertices. The ligand-receptor similarity graph construction module is further configured to determine whether each edge exists. Specifically, the ligand-receptor similarity graph construction module is further configured to determine whether there is an edge between any two vertices of the plurality of vertices by a distance between the two vertices. The ligand-receptor similarity graph construction module includes a first distance determination module, a second distance determination module, and an edge determination module. The first distance determination module is configured to determine a first distance between a point in a ligand graph at a first vertex and a point in a ligand graph at a second vertex. The second distance determination module is configured to determine a second distance between a point in a receptor graph at the first vertex and a point in a receptor graph at the second vertex. The edge determination module is configured to determine that, when both the first distance and the second distance are less than a preset distance, the edge between any two vertices is added. The pharmacophore model 912 is configured to construct a pharmacophore model based on the ligand-receptor similarity graph to determine whether the selected drug molecule could inhibit activity of the selected receptor. The pharmacophore model is further configured to calculate a maximum weight clique between the selected drug molecule and the selected receptor to screen a drug molecule compound.

The molecular docking method based on a CIM according to the embodiment of the present disclosure is described in detail below with reference to the drawings and specific examples.

In the present disclosure, the important molecular docking problem in the drug screening process is transformed into a quadratic unconstrained binary optimization (QUBO) model through the CIM. A user can convert a 3D molecular model into a mathematical graph to represent the ligand and receptor and use the QUBO model to predict a ligand-receptor binding mode through mathematical modeling. The user can upload different micromolecules and protein structures, which will be converted by a server in a later stage. The CIM will provide an optimal calculation result and display the 3D model to the user. In the drug screening problem, the CIM is faster and more accurate than traditional computers.

1. Molecular display

Firstly, molecular display is conducted to display the 3D molecular structure (crystal structure or structure after energy minimization) obtained by the present disclosure. Then, the 3D molecular structure of the molecule is simplified into a mathematical graph, and the simplified structure is displayed as weighted graphs $G_L$ and $G_P$ of distance matrices/edges.

2. Construction of internal pseudo-atom point diagram of receptor target

A series of pseudo-atom points is generated through AutoSite to represent a possible maximum atom point diagram within a receptor target region.

3. Construction of ligand-receptor similarity graph

According to the above steps, the receptor graph and the ligand graph are constructed to obtain the ligand-receptor similarity graph G, with a set of points as follows:

$$G = (V, E),$$

$$V = V_L \times V_P = \{x_{(i,j)}\}_{i=1,\ldots,m}^{j=1,\ldots,n}$$

where $V_P$ is a point in the receptor graph, $V_L$ is a point in the ligand graph, and the weight of $x_{(i,j)}$ in the ligand-receptor similarity graph is determined by an atom type represented by i and j.

The edge between the vertices $x_{(i,j)}$ and $x_{(k,l)}$ in the ligand-receptor similarity graph (i.e., binding interaction graph) is determined by the distance between (i,k) and (j,l). If the distance between (i,k) and (j,l) is less than 0.5 angstroms, then it is determined that there is an edge between these two vertices, otherwise there is none.

Subsequently, the problem is simplified to finding a maximum clique in the ligand-receptor similarity graph. For any graph G=(V,E), if U⊆V and if, for any two vertices u,v ∈ U, |u,v|∈ E, then U is a complete subgraph of G, and the complete subgraph of G is a clique of G. The maximum clique of G refers to the maximum complete subgraph of G. The problem of finding the maximum clique of any graph is a non-deterministic polynomial-time hardness (NP-hard) problem. The similarity of atoms between the ligand and the receptor corresponding to the maximum clique in the inter-action graph is a weight-based optimal docking method (the weight is calculated based on historical data, and the quality of the final optimal docking depends on the quality of the weight calculation method).

4. Mathematical model

The ligand graph is expressed by:

$$G_L = (V_L, E_L),$$

$$|V_L| = m$$

The receptor graph is expressed by:

$$| G_P = (V_P, E_P),$$

$$|V_P| = n$$

The ligand-receptor similarity graph is expressed by:

$$G = (V, E),$$

$$V = V_L \times V_P = \{x_{(i,j)}\}_{i=1,\ldots,m}^{j=1,\ldots,n}$$

It is necessary to maximize:

$$\sum_{i=1}^{m}\sum_{j=i}^{n} w_{(i,j)} x_{(i,j)} - K_1 \sum_{i,k=1}^{m}\sum_{j,l=1}^{n} w_{(i,j),(k,l)} x_{(i,j)}$$

The solution satisfies the constraint condition (each atom of the ligand/receptor can overlap with at most one atom of the receptor/ligand), where $w_{(i,j)}$ denotes the weight of the vertex $x_{(i,j)}$, depending on the type of the atom/group to which i, j corresponds.

$w_{(i,j),(k,l)}$ denotes the weight of the edge between $x_{(i,j)}$ and $x_{(k,l)}$ in the ligand-receptor similarity graph. If $x_{(i,j)}$ and $x_{(k,l)}$ are connected by an edge, then $w_{(i,j),(k,l)}$=L If $x_{(i,j)}$ and $x_{(k,l)}$ are not connected by an edge, then $w_{(i,j),(k,l)}$=0. Whether $x_{(i,j)}$ and $x_{(k,l)}$ are connected by an edge depends on the distance between (i,j) and (k,l).

The problem is converted into a QUBO model. In the following equation, $K_1$ is the coefficient of the maximum weight clique, $K_2$ and $K_3$ are Lagrange coefficients used to constrain the number of connections of a node and the number of solutions.

$$\min\left(-\sum_{i=1}^{m}\sum_{j=1}^{n} w_{(i,j)} x_{(i,j)} + K_1 \sum_{i,k=1}^{m}\sum_{j,l=1}^{n} w_{(i,j),(k,l)} x_{(i,j)} + K_2 \sum_{i=1}^{m}(\sum_{j=1}^{n} x_{(i,j)} - s_1\right)^2 +$$

$$K_2 \sum_{j=1}^{m}(\sum_{i=1}^{n} x_{(i,j)} - s_1\right)^2\right) + K_3 \left(\sum_{i=1}^{m}\sum_{j=1}^{n} x_{(i,j)} - (s_3 + 2s_4 + 4S_5 + 3)\right)^2\right)$$

Figure 8:
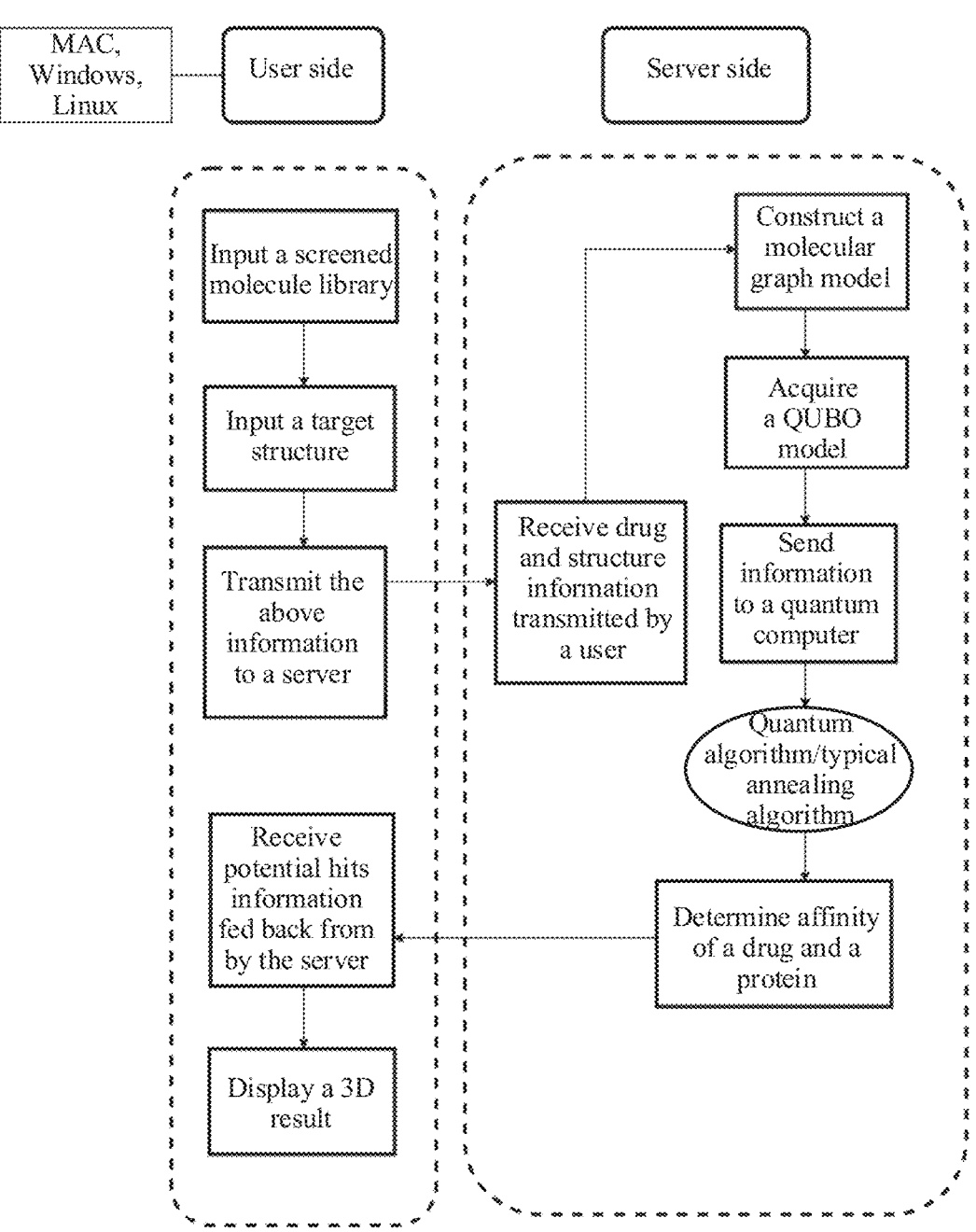
FIG. 8 an overall flowchart of the molecular docking method based on a CIM according to an embodiment of the present disclosure.

5. As shown in FIG. 8, when in use, the user only needs to input a screened drug library file and target protein structure file. A user side will display their initial structure and pharmacophore structure, making it easy for the user to perform visualized 3D operations. Then, after a target range is determined, the data is transmitted to the server. The server constructs a QUBO model based on the above parameters and transmits it to the CIM (also known as a quantum computer) to obtain an optimal solution. Due to the use of the quantum computer, the time taken by the entire process is greatly reduced, and the user can see the screened structural model and score on a user interface. Subsequently, the molecule is used for further experimental validation to obtain a lead compound.

Figure 19:
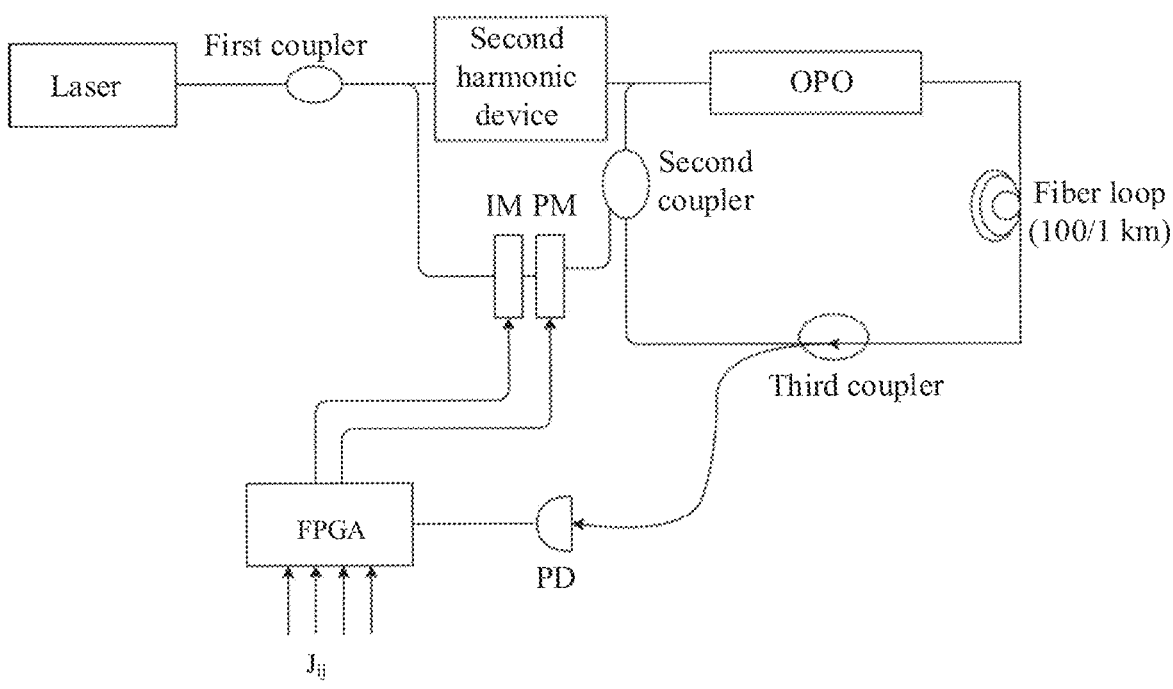
FIG. 19 is a hardware diagram of a quantum computer.

As shown in FIG. 19, a laser serves as a pump light source, and a first coupler divides light into two beams. One beam is frequency doubled by a second harmonic device crystal, and the other beam is used as injection light. The doubled light is injected into a fiber loop, while exciting an optical parametric oscillator (OPO) for optical parametric oscillation to generate vacuum compressed optical pulses. The optical pulses circulate in a fiber loop. At a third coupler side, a portion of the light undergoes zero difference frequency detection to obtain compressed phase information of the optical pulse as a partial input to a field programmable gate array (FPGA). The data to be calculated ($J_{ij}$) is input into the FPGA as programming data. A computing unit outputs modulation signals to an intensity modulator (IM) and a phase modulator (PM). A beam of light from the first coupler passes through the IM and PM and re-enters the fiber loop through the second coupler to achieve pulse injection. After the calculation begins, the power of the pump laser gradually increases. According to the principle of minimum gain, pulse signals that interact with each other will undergo a phase transition, resulting in a phase collapse. Through the measurement of a photodetector (PD), a calculation result of combination optimization that meets the input $J_{ij}$ design is obtained.

In a First Example, a Structure of an MMP9-Inhibitor Complex is Obtained as Follows.

Figure 10A:
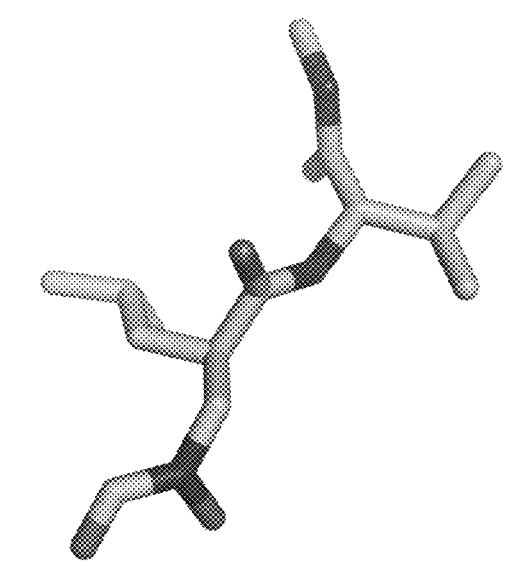
FIG. 10A is a schematic diagram of a ligand structure according to the first specific example of the present disclosure.
Figure 10B:
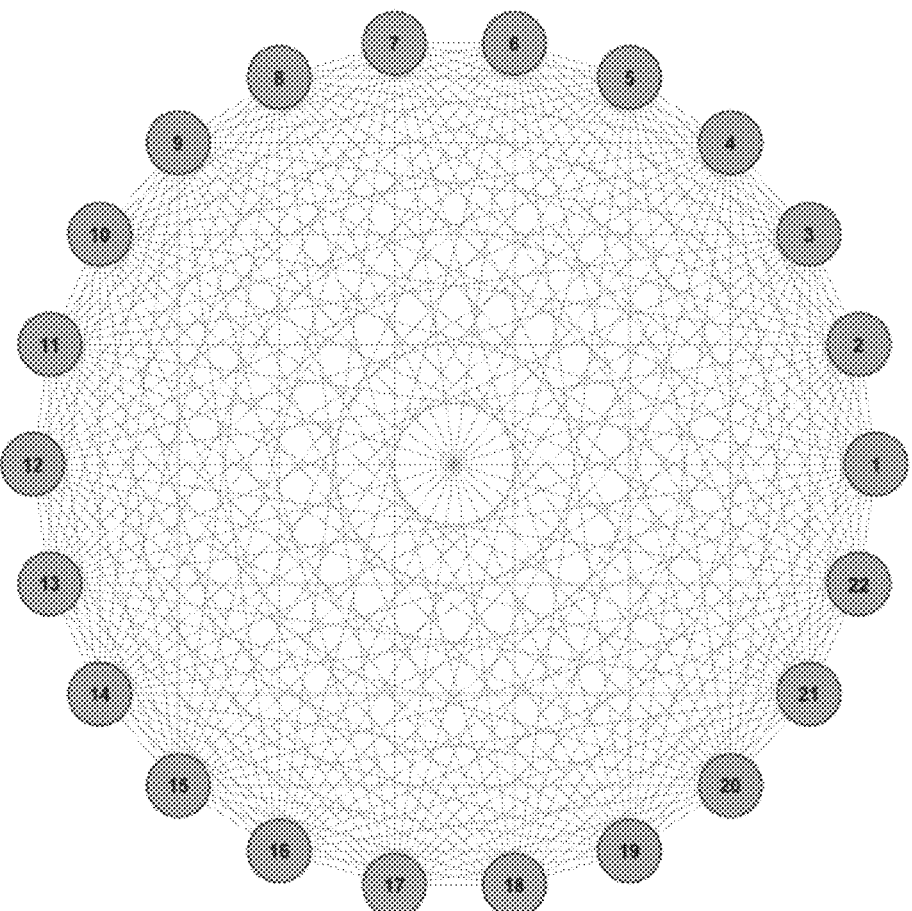
FIG. 10B is a ligand graph according to the first specific example of the present disclosure.

(1) An inhibitor of MMP9 is selected from the drug molecule library to be screened, and a 3D molecular structure diagram (as shown in FIG. 10A) is constructed based on the inhibitor of MMP9. Then, a ligand graph is obtained based on the 3D molecular structure diagram (as shown in FIG. 10B). The ligand graph includes 22 atoms in the 3D molecular structure diagram and a plurality of edges between any two atoms, with each edge being an edge between any two of the 22 atoms.

(2) The MMP9 is selected from the receptor library. Based on the MMP9, a pseudo-atom diagram (as shown in FIG. 11A) is obtained through AutoSite. Then, based on the pseudo-atom diagram, a receptor graph (as shown in FIG. 11B) is constructed. The receptor graph includes 51 atoms and a plurality of edges between any two atoms, with each edge being an edge between any two of the 51 atoms.

(3) Vertices in the ligand-receptor similarity graph are constructed based on the ligand graph and the receptor graph, with some vertices shown in Table 1.

TABLE 1

| L1, R1 | L2, R1 | L3, R1 | L4, R1 |
| L1, R2 | L2, R2 | L3, R2 | L4, R2 |

TABLE 1-continued

| L1, R3 | L2, R3 | L3, R3 | L4, R3 |
| L1, R4 | L2, R4 | L3, R4 | L4, R4 |
| L1, R5 | L2, R5 | L3, R5 | L4, R5 |
| L1, R6 | L2, R6 | L3, R6 | L4, R6 |
| L1, R7 | L2, R7 | L3, R7 | L4, R7 |
| L1, R8 | L2, R8 | L3, R8 | L4, R8 |
| L1, R9 | L2, R9 | L3, R9 | L4, R9 |
| L1, R10 | L2, R10 | L3, R10 | L4, R10 |

(4) Weights are assigned to the points in the graph, which may have different parameter combinations, one of which is shown in Table 2.

TABLE 2

| Weight related table | | | |
|---|---|---|---|
| | | receptor | |
| Ligand | C | O | H |
| C | 1 | 1 | 0.1 |
| N | 0.9 | 1.5 | 0.1 |
| O | 0.8 | 2 | 0.1 |
| P | 0.5 | 1 | 0.1 |
| H | 0.1 | 0.1 | 1 |
| Cl | 0.4 | 0.9 | 0.1 |
| S | 0.4 | 1.5 | 0.1 |
| F | 0.6 | 0.9 | 0.1 |

(5) It is determined whether there is an edge between points in the graph according to the following criteria.

To determine whether there is an edge between the nodes (i.e. the vertices mentioned earlier) R. A(L1,R2) and B(L2, R2), it is determined whether a distance between (L1, L2) and (R1, R2) is within a range of 0.1 angstroms-2 angstroms. If yes, there is an edge between the node A(L1,R2) and the node B(L2,R2). If the distance is greater than 2 angstroms, there is no edge between these two points.

(6) A QUBO mode matrix is constructed and solved.

(7) Pairings [('12','r45'), ('14','r25'), ('18','r31'), ('110', 'r25'), ('113','r45'), ('114','r18'), ('115','r11'), ('116', 'r28'), ('117','r39'), ('118','r37'), ('119','r28'), ('120', 'r16')] are output to obtain a maximum weight clique.

(8) A 3D structure is obtained through a Kabsch rotation matrix.

Figure 12:
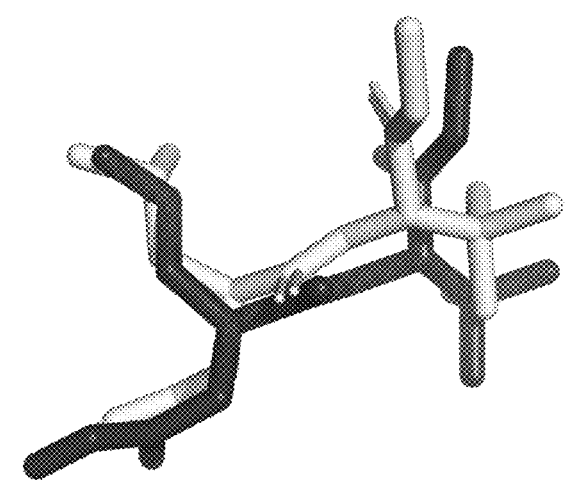
FIG. 12 is a 3D structure diagram after MMP9 and its inhibitor are docked according to the first specific example of the present disclosure.

The obtained result is compared with an original result. As shown in FIG. 12, an original ligand structure marked gray and a docked ligand structure marked black have little difference.

In a Second Example, a Structure of a Mouse Thiamine Pyrophosphokinase and Thiamine Complex is Obtained as Follows.

Figure 13A:
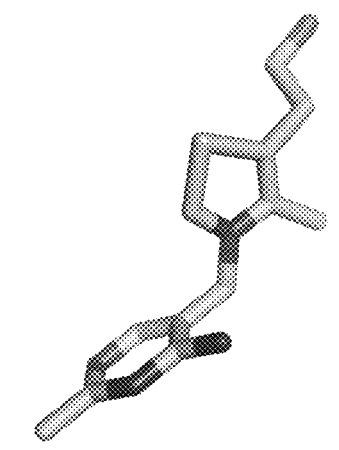
FIG. 13A is a schematic diagram of a ligand structure according to a second specific example of the present disclosure.
Figure 13B:
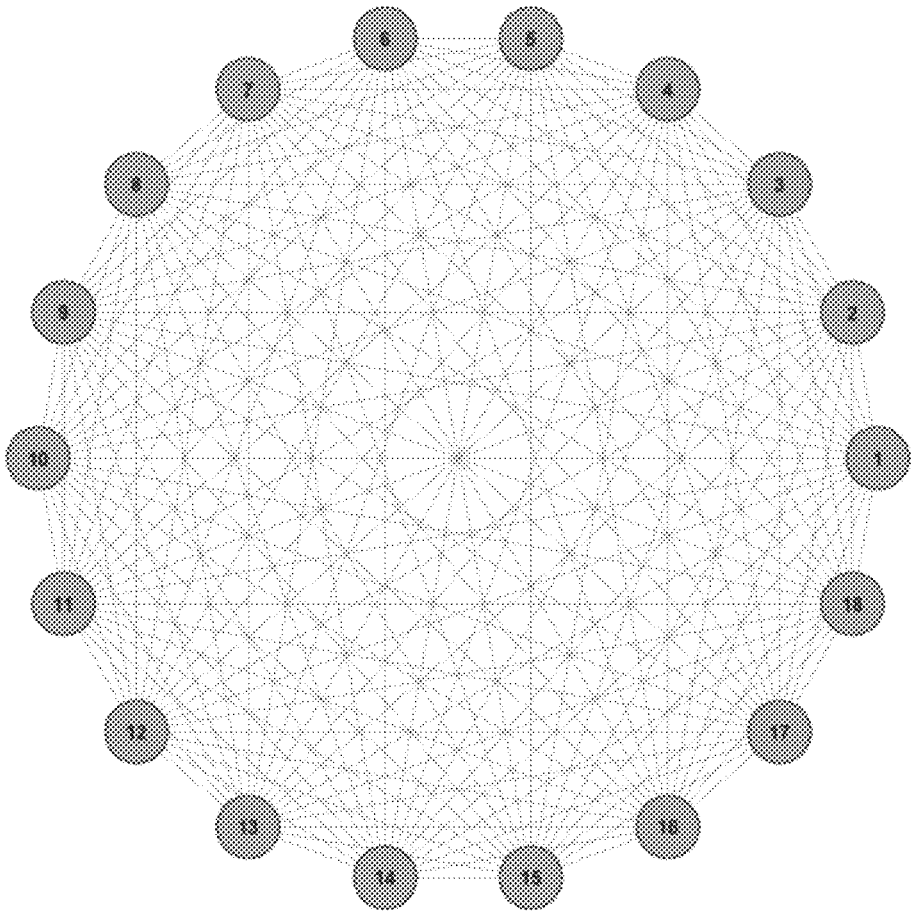
FIG. 13B is a ligand graph according to the second specific example of the present disclosure.

(1) The thiamine is selected from the drug molecule library to be screened, and a 3D molecular structure diagram (as shown in FIG. 13A) is constructed based on the thiamine. Then, a ligand graph is obtained based on the 3D molecular structure diagram (as shown in FIG. 13B). The ligand graph includes 18 atoms in the 3D molecular structure diagram and a plurality of edges between any two atoms, with each edge being an edge between any two of the 18 atoms.

(2) The mouse thiamine pyrophosphokinase is selected from the receptor library. Based on the mouse thiamine pyrophosphokinase, a pseudo-atom diagram (as shown in FIG. 14A) is obtained through AutoSite. Then, based on the pseudo-atom diagram, a receptor graph (as shown in FIG. 14B) is constructed. The receptor graph includes 54 atoms and a plurality of edges between any two atoms, with each edge being an edge between any two of the 54 atoms.

(3) Vertices in the ligand-receptor similarity graph are constructed based on the ligand graph and the receptor graph, with some vertices shown in Table 3.

TABLE 3

| L1, R1 | L2, R1 | L3, R1 | L4, R1 |
| L1, R2 | L2, R2 | L3, R2 | L4, R2 |
| L1, R3 | L2, R3 | L3, R3 | L4, R3 |
| L1, R4 | L2, R4 | L3, R4 | L4, R4 |
| L1, R5 | L2, R5 | L3, R5 | L4, R5 |
| L1, R6 | L2, R6 | L3, R6 | L4, R6 |
| L1, R7 | L2, R7 | L3, R7 | L4, R7 |
| L1, R8 | L2, R8 | L3, R8 | L4, R8 |
| L1, R9 | L2, R9 | L3, R9 | L4, R9 |
| L1, R10 | L2, R10 | L3, R10 | L4, R10 |

(4) Weights are assigned to the points in the graph, which may have different parameter combinations, one of which is shown in Table 4.

TABLE 4

Weight related table

| | rec | | |
| lig | C | O | H |
|---|---|---|---|
| C | 1 | 1 | 0.1 |
| N | 0.9 | 1.5 | 0.1 |
| O | 0.8 | 2 | 0.1 |
| P | 0.5 | 1 | 0.1 |
| H | 0.1 | 0.1 | 1 |
| Cl | 0.4 | 0.9 | 0.1 |
| S | 0.4 | 1.5 | 0.1 |
| F | 0.6 | 0.9 | 0.1 |

(5) It is determined whether there is an edge between points in the graph according to the following criteria.

To determine whether there is an edge between the nodes A(L1,R2) and B(L2,R2), it is determined whether a distance between (L1, L2) and (R1, R2) is within a range of 0.1 angstroms-2 angstroms. If yes, there is an edge between the node A(L1,R2) and the node B(L2,R2). If the distance is greater than 2 angstroms, there is no edge between these two points.

(6) A QUBO mode matrix is constructed and solved.

(7) Pairings ('l3','r4'), ('l5','r37'), ('l6','r18'), ('l6', 'r51'), ('l8','r35'), ('l10','r20'), ('l11','r42'), ('l13', 'r20'), and ('l15','r21') are output to obtain a maximum weight clique.

(8) A 3D structure is obtained through a Kabsch rotation matrix.

Figure 15:
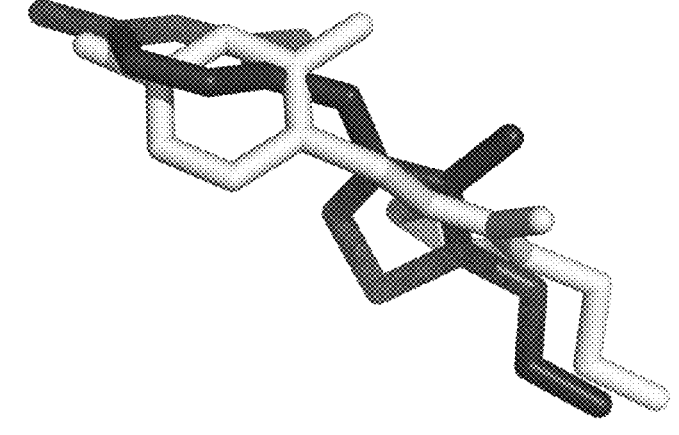
FIG. 15 is a 3D structure diagram after mouse thiamine pyrophosphokinase and thiamine are docked according to the second specific example of the present disclosure.

The obtained result is compared with an original result. As shown in FIG. 15, an original ligand structure marked gray and a docked ligand structure marked black have little difference.

In a Third Example, a Structure of IMP-1 Metallo-β-Lactamase from *Pseudomonas Aeruginosa* and Biaryl Succinic Acid Inhibitor Complex (11) is Obtained as Follows.

Figure 16A:
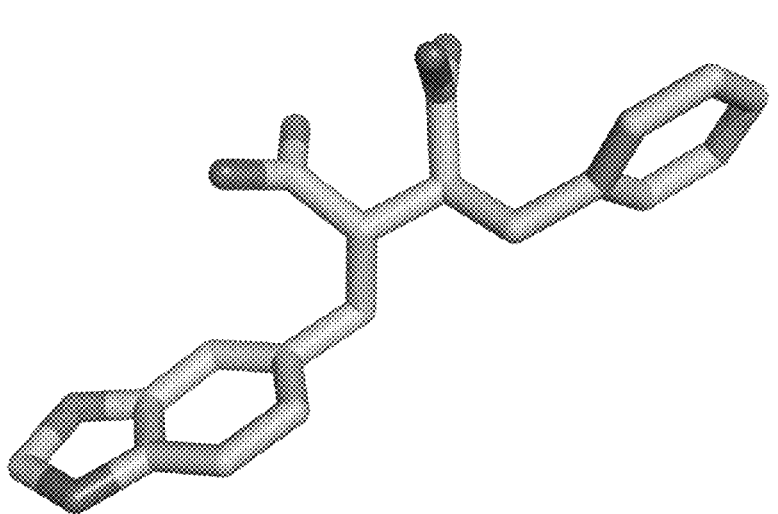
FIG. 16A is a schematic diagram of a ligand structure according to a third specific example of the present disclosure.
Figure 16B:
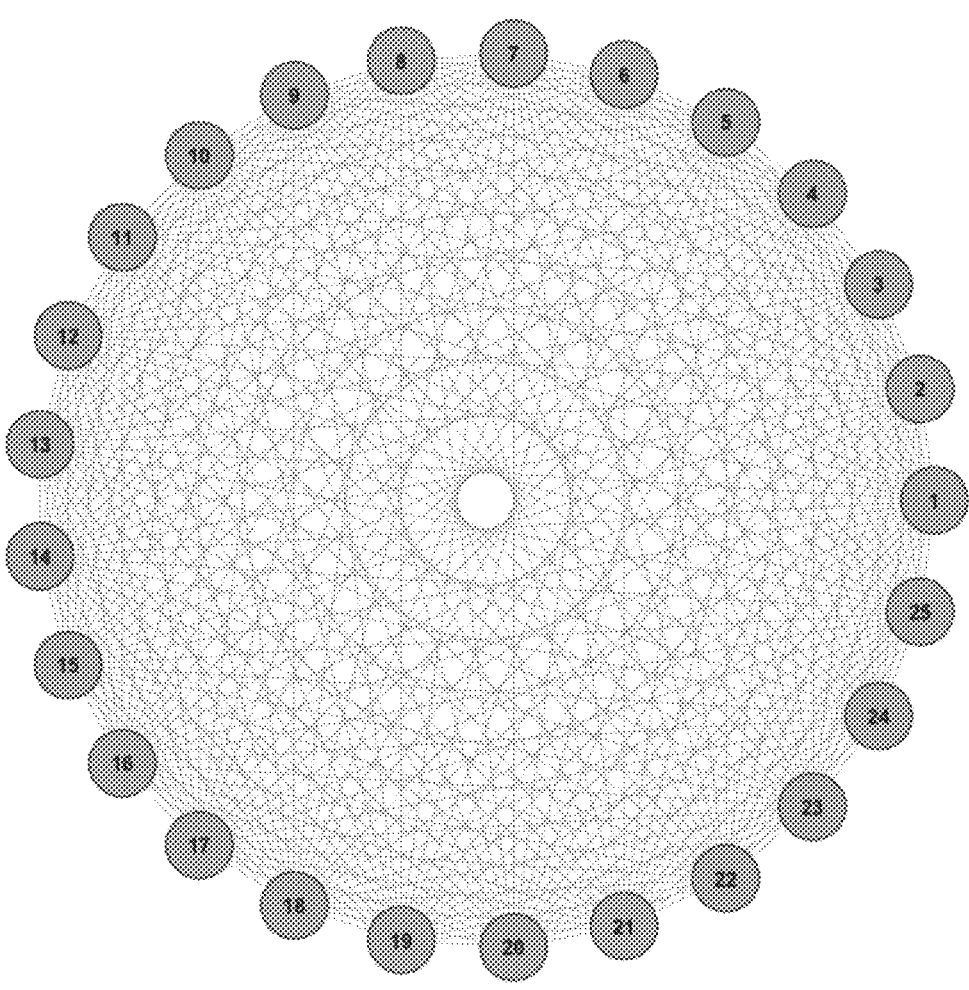
FIG. 16B is a ligand graph according to the third specific example of the present disclosure.

(1) The biaryl succinic acid inhibitor complex (11) is selected from the drug molecule library to be screened, and a 3D molecular structure diagram (as shown in FIG. 16A) is constructed based on the biaryl succinic acid inhibitor complex (11). Then, a ligand graph is obtained based on the 3D molecular structure diagram (as shown in FIG. 16B). The ligand graph includes 25 atoms in the 3D molecular structure diagram and a plurality of edges between any two atoms, with each edge being an edge between any two of the 25 atoms.

(2) The IMP-1 metallo-β-lactamase from *Pseudomonas aeruginosa* is selected from the receptor library. Based on the IMP-1 metallo-β-lactamase from *Pseudomonas aeruginosa*, a pseudo-atom diagram (as shown in FIG. 17A) is obtained through AutoSite. Then, based on the pseudo-atom diagram, a receptor graph (as shown in FIG. 17B) is constructed. The receptor graph includes 23 atoms and a plurality of edges between any two atoms, with each edge being an edge between any two of the 23 atoms.

(3) Vertices in the ligand-receptor similarity graph are constructed based on the ligand graph and the receptor graph, with some vertices shown in Table 5.

TABLE 5

| L1, R1 | L2, R1 | L3, R1 | L4, R1 |
| L1, R2 | L2, R2 | L3, R2 | L4, R2 |
| L1, R3 | L2, R3 | L3, R3 | L4, R3 |
| L1, R4 | L2, R4 | L3, R4 | L4, R4 |
| L1, R5 | L2, R5 | L3, R5 | L4, R5 |
| L1, R6 | L2, R6 | L3, R6 | L4, R6 |
| L1, R7 | L2, R7 | L3, R7 | L4, R7 |
| L1, R8 | L2, R8 | L3, R8 | L4, R8 |
| L1, R9 | L2, R9 | L3, R9 | L4, R9 |
| L1, R10 | L2, R10 | L3, R10 | L4, R10 |

(4) Weights are assigned to the points in the graph, which may have different parameter combinations, one of which is shown in Table 6.

TABLE 6

Weight related table

| | receptor | | |
| Ligand | C | O | H |
|---|---|---|---|
| C | 1 | 1 | 0.1 |
| N | 0.9 | 1.5 | 0.1 |
| O | 0.8 | 2 | 0.1 |
| P | 0.5 | 1 | 0.1 |
| H | 0.1 | 0.1 | 1 |
| Cl | 0.4 | 0.9 | 0.1 |
| S | 0.4 | 1.5 | 0.1 |
| F | 0.6 | 0.9 | 0.1 |

(5) It is determined whether there is an edge between points in the graph according to the following criteria.

To determine whether there is an edge between the nodes A(L1,R2) and B(L2,R2), it is determined whether a distance between (L1, L2) and (R1, R2) is within a range of 0.1 angstroms-2 angstroms. If yes, there is an edge between the node A(L1,R2) and the node B(L2,R2). If the distance is greater than 2 angstroms, there is no edge between these two points.

(6) A QUBO mode matrix is constructed and solved.

(7) Pairings [('l0','r11'), ('l2','r20'), ('l5','r16'), ('l6', 'r19'), ('l9','r21'), ('l17','r12'), ('l19','r3'), and ('l21', 'r3')] are output to obtain a maximum weight clique.

(8) A 3D structure is obtained through a Kabsch rotation matrix.

Figure 18:
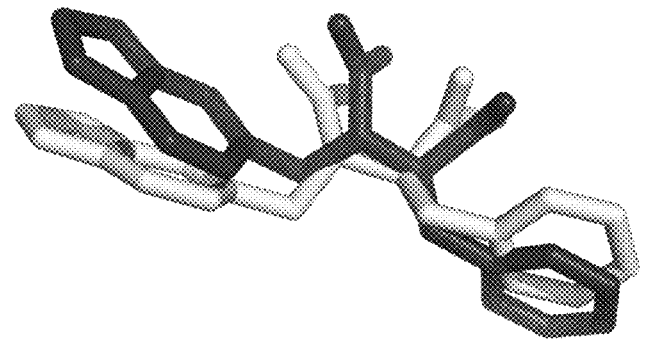
FIG. 18 is a 3D structure diagram after IMP-1 metallo-β-lactamase from *Pseudomonas aeruginosa* and a biaryl succinic acid inhibitor are docked according to the third specific example of the present disclosure.

The obtained result is compared with an original result. As shown in FIG. 18, an original ligand structure marked gray and a docked ligand structure marked black have little difference.

Key Points of the Present Disclosure

The present disclosure develops a computing device for drug screening. It uses a quantum computer for acceleration and can quickly calculate the affinity between a drug and a protein to help researchers screen a potential lead compound, thereby assisting in the drug development process.

Advantages of the Present Disclosure

Compared with traditional molecular docking models, the model of the present disclosure solves the problem that heuristic algorithms may are time-consuming but are unable to obtain standard solutions. In the present disclosure, the method of solving molecular simulation problems through the Ising model is faster and more accurate. Based on the entanglement and overlapping states and fully connected characteristics of the quantum computer, the present disclosure proposes a more excellent model for solving molecular binding modes. The model is displayed on the web and available for users to use. In the pharmaceutical field, the present disclosure is more convenient and fast, and can obtain better potential pharmaceutical compounds.

Compared with the prior art, the present disclosure can directly obtain the POSE of the ligand-receptor structure, i.e. the 3D pose in the bound state.

Those skilled in the art can understand that relevant hardware can be instructed through computer programs to implement all or part of processes in the method according to the above embodiments, and the programs can be stored in a computer-readable storage medium. The computer-readable storage medium may be a magnetic disk, an optical disk, a read-only memory (ROM), a random access memory (RAM), or the like.

The above merely describes preferred specific implementations of the present disclosure, but a protection scope of the present disclosure is not limited thereto. Any person skilled in the art can easily conceive modifications or replacements within the technical scope of the present disclosure, and these modifications or replacements shall fall within the protection scope of the present disclosure.

What is claimed is:

1. A method for screening a lead drug molecule compound based on a molecular docking simulation performed by a coherent Ising machine (CIM), comprising:

selecting a drug molecule from a drug molecule library to be screened, and constructing a three-dimensional (3D) molecular structure diagram based on the selected drug molecule to obtain a ligand graph;

selecting a receptor from a receptor library, and constructing an internal pseudo-atom point diagram of a receptor target based on the selected receptor molecule to obtain a receptor graph;

constructing a ligand-receptor similarity graph based on the ligand graph and the receptor graph, wherein the ligand-receptor similarity graph comprises a plurality of vertices and edges, any vertex of the plurality of vertices comprises a point in the ligand graph and a point in the receptor graph, and there is an edge between any two vertices; and determining whether each edge exists by determining whether there is an edge between any two vertices of the plurality of vertices by a distance between the two vertices comprising determining a first distance between a point in a ligand graph at a first vertex and a point in a ligand graph at a second vertex;

determining a second distance between a point in a receptor graph at the first vertex and a point in a receptor graph at the second vertex; and determining that, when the first distance and the second distance are less than a preset distance, the edge between any two vertices is added;

constructing a pharmacophore model based on the ligand-receptor similarity graph, wherein the pharmacophore model is performed by a CIM configured to calculate a maximum weight clique between the selected drug molecule and the selected receptor to screen a drug molecule compound, wherein the maximum weight clique between the selected drug molecule and the selected receptor is determined according to a following equation:

$$\sum_{i=1}^{m}\sum_{j=i}^{n}w_{(i,j)}x_{(i,j)} - K_1\sum_{i,k=1}^{m}\sum_{j,l=1}^{n}w_{(i,j),(k,l)}x_{(i,j)}$$

wherein $w_{(i,j)}$ denotes the weight of a vertex $x_{(i,j)}$ in the ligand-receptor similarity graph, depending on a type of an atom/group corresponding to i,j; $w_{(i,j),(k,l)}$ denotes the weight of an edge between $x_{(i,j)}$ and $x_{(k,l)}$ in the ligand-receptor similarity graph; and $K_1$ is coefficient of the maximum weight clique; and constructing a 3D structure from the pharmacophore model to determine whether the selected drug molecule could inhibit the activity of the selected receptor, wherein the 3D structure is the 3D pose of the ligand-receptor structure in the bound state.

2. The method according to claim 1, wherein the preset distance is within a range of 0.1 angstroms-2 angstroms.

3. The method according to claim 1, wherein the maximum weight clique between the selected drug molecule and the selected receptor corresponds to a similarity of atoms between the selected drug molecule and the selected receptor.

4. The method according to claim 1, wherein the pharmacophore model is solved according to a following equation:

$$\min\left(-\sum_{i=1}^{m}\sum_{j=1}^{n}w_{(i,j)}x_{(i,j)} + K_1\sum_{i,k=1}^{m}\sum_{j,l=l}^{n}w_{(i,j),(k,l)}x_{(i,j)} + K_2\sum_{i=1}^{m}\left(\sum_{j=1}^{n}x_{(i,j)} - s_1\right)^2 + \right.$$
$$\left. K_2\sum_{j=1}^{m}\left(\sum_{i=1}^{n}x_{(i,j)} - s_1\right)^2\right) + K_3\left(\sum_{i=1}^{m}\sum_{j=1}^{n}x_{(i,j)} - (s_3 + 2s_4 + 4S_5 + 3)\right)^2\right)$$

wherein $w_{(i,j)}$ denotes the weight of the vertex $x_{(i,j)}$ in the ligand-receptor similarity graph, depending on the type of the atom/group corresponding to i,j; $w_{(i,j),(k,l)}$ denotes the weight of the edge between $x_{(i,j)}$ and $x_{(k,l)}$ in the ligand-receptor similarity graph; $K_1$ is the coefficient of the maximum weight clique; and $K_2$ and $K_3$ are Lagrange coefficients used to constrain a number of connections of a node and a number of solutions.

5. The method according to claim 1, wherein the selected receptor comprises a protein, a nucleic acid or a polysaccharide; and the selected drug molecule comprises aspirin, oseltamivir or remdesivir.

6. The method according to claim 1, wherein data to be calculated ($J_{ij}$) is input into a field-programmable gate array (FPGA) of the CIM depending on a plurality of the type of atom/group corresponding to i,j; and a power of a pump laser of the CIM is increased according to the internal pseudo-atom point diagram of the receptor target.

7. An apparatus for simulating molecular docking based on a coherent Ising machine (CIM) computing output, comprising:

a ligand selection module, configured to select a drug molecule from a drug molecule library to be screened;

a ligand graph construction module, configured to construct a 3D molecular structure diagram based on the selected drug molecule to obtain a ligand graph;

a receptor selection module, configured to select a receptor from a receptor library;

a receptor graph construction module, configured to construct an internal pseudo-atom point diagram of a receptor target based on the selected receptor molecule to obtain a receptor graph;

a ligand-receptor similarity graph construction module, configured to construct a ligand-receptor similarity graph based on the ligand graph and the receptor graph, wherein the ligand-receptor similarity graph comprises a plurality of vertices and edges, any vertex of the plurality of vertices comprises a point in the ligand graph and a point in the receptor graph, and there is an edge between any two vertices; and the ligand-receptor similarity graph construction module is further configured to determine whether each edge exists; and a pharmacophore model, performed by a CIM configured to construct a pharmacophore model based on the ligand-receptor similarity graph to determine whether the selected drug molecule could inhibit activity of the selected receptor, wherein the pharmacophore model is configured to calculate a maximum weight clique between the selected drug molecule and the selected receptor to screen a drug molecule compound and construct a 3D pose of the ligand-receptor structure in the bound state from the pharmacophore model, wherein the maximum weight clique between the selected drug molecule and the selected receptor is determined according to a following equation:

$$\sum_{i=1}^{m}\sum_{j=i}^{n} w_{(i,j)} x_{(i,j)} - K_1 \sum_{i,k=1}^{m}\sum_{j,l=1}^{n} w_{(i,j),(k,l)} x_{(i,j)}$$

wherein $w_{(i,j)}$ denotes the weight of a vertex $x_{(i,j)}$ in the ligand-receptor similarity graph, depending on a type of an atom/group corresponding to i,j; $w_{(i,j),(k,l)}$ denotes the weight of an edge between $x_{(i,j)}$ and $x_{(k,l)}$ in the ligand-receptor similarity graph; and $K_1$ is coefficient of the maximum weight clique.

8. The apparatus according to claim 7, wherein the ligand-receptor similarity graph construction module is further configured to determine whether there is an edge between any two vertices of the plurality of vertices by a distance between the two vertices; and the ligand-receptor similarity graph construction module comprises a first distance determination module, a second distance determination module, and an edge determination module;

the first distance determination module is configured to determine a first distance between a point in a ligand graph at a first vertex and a point in a ligand graph at a second vertex;

the second distance determination module is configured to determine a second distance between a point in a receptor graph at the first vertex and a point in a receptor graph at the second vertex; and the edge determination module is configured to determine that, when the first distance and the second distance are less than a preset distance, the edge between any two vertices is added.

9. The apparatus according to claim 7, wherein the pharmacophore model is solved according to a following equation:

$$\min\left( -\sum_{i=1}^{m}\sum_{j=1}^{n} w_{(i,j)} x_{(i,j)} + K_1 \sum_{i,k=1}^{m}\sum_{j,l=l}^{n} w_{(i,j),(k,l)} x_{(i,j)} + K_2 \sum_{i=1}^{m}\left(\sum_{j=1}^{n} x_{(i,j)} - s_1\right)^2 + \right.$$
$$\left. K_2 \sum_{j=1}^{m}\left(\sum_{i=1}^{n} x_{(i,j)} - s_1\right)^2 + K_3\left(\sum_{i=1}^{m}\sum_{j=1}^{n} x_{(i,j)} - (s_3 + 2s_4 + 4S_5 + 3)\right)^2\right)$$

wherein $w_{(i,j)}$ denotes the weight of the vertex $x_{(i,j)}$ in the ligand-receptor similarity graph, depending on the type of the atom/group corresponding to i,j; $w_{(i,j),(k,l)}$ denotes the weight of the edge between $x_{(i,j)}$ and $x_{(k,l)}$ in the ligand-receptor similarity graph; $K_1$ is the coefficient of the maximum weight clique; and $K_2$ and $K_3$ are Lagrange coefficients used to constrain a number of connections of a node and a number of solutions.

* * * * *